(12) United States Patent
Chmiel et al.

(10) Patent No.: US 8,764,654 B2
(45) Date of Patent: Jul. 1, 2014

(54) DATA ACQUISITION FOR MODULAR BIOMETRIC MONITORING SYSTEM

(75) Inventors: Alan J. Chmiel, Avon Lake, OH (US); Bradley T. Humphreys, Lakewood, OH (US); Carlos M. Grodsinsky, Hinkley, OH (US)

(73) Assignee: Zin Technologies, Inc., Middleburg Heights, OH (US)

( * ) Notice: Subject to any disclaimer, the term of this patent is extended or adjusted under 35 U.S.C. 154(b) by 1565 days.

(21) Appl. No.: 12/051,019

(22) Filed: Mar. 19, 2008

(65) Prior Publication Data

US 2009/0240117 A1    Sep. 24, 2009

(51) Int. Cl.
| | | |
|---|---|---|
| *A61B 5/00* | (2006.01) | |
| *G06F 13/18* | (2006.01) | |
| *G06F 13/26* | (2006.01) | |
| *G06F 13/38* | (2006.01) | |
| *G06F 13/42* | (2006.01) | |
| *G06F 12/06* | (2006.01) | |
| *G06F 5/12* | (2006.01) | |
| *G06F 3/05* | (2006.01) | |
| *G06F 19/00* | (2011.01) | |
| *G06F 13/00* | (2006.01) | |
| *G06F 12/00* | (2006.01) | |
| *G06F 5/00* | (2006.01) | |

(52) U.S. Cl.
CPC ............ *G06F 19/3418* (2013.01); *G06F 19/36* (2013.01); *G06F 13/18* (2013.01); *G06F 13/26* (2013.01); *G06F 13/38* (2013.01); *G06F 13/4213* (2013.01); *G06F 13/4226* (2013.01); *G06F 13/4239* (2013.01); *G06F 12/0623* (2013.01); *G06F 5/12* (2013.01); *A61B 5/0002* (2013.01); *G06F 3/05* (2013.01); *A61B 2505/01* (2013.01); *A61B 2505/07* (2013.01); *A61B 2560/0475* (2013.01); *Y10S 128/92* (2013.01)
USPC ........... 600/301; 711/151; 711/158; 709/248; 709/243; 709/244; 710/57; 705/2; 705/3; 128/920

(58) Field of Classification Search
CPC ..... G06F 13/18; G06F 13/1605; G06F 13/26; G06F 12/0623; G06F 13/4239; G06F 13/4226; G06F 19/3418; G06F 19/36; G06F 5/12; G06F 13/4213; A61B 5/0002; A61B 2505/01; A61B 2560/0475; A61B 2505/07; A61B 2560/04; A61B 2560/045
USPC ......... 600/300–301, 309, 319, 320, 316, 322, 600/344–361, 372–390, 393; 709/201–253, 709/200; 439/1–75, 76.1, 76.2, 77–268, 439/269.1, 269.2, 270–475, 476.1, 439/477–538, 539, 540.1, 541, 541.5, 439/542–606, 620.01–620.34, 623–697; 710/1–74, 100, 300–304, 305–317, 710/104–125; 712/1–43; 707/688; 705/2–3
See application file for complete search history.

(56) References Cited

U.S. PATENT DOCUMENTS 3,553,651 A * 1/1971 Bird et al. .................... 711/219

(Continued)

OTHER PUBLICATIONS

Matthews, R et al. "A Wearable Physiological Sensor Suite for Unobtrusive Monitoring of Physiological and Cognitive State", Proceedings of the 29th Annual International Conference of the IEEE EMBS, Cité Internationale, Lyon, France, Aug. 23-26, 2007, p. 5276-5281.*

(Continued)

*Primary Examiner* — Gary Jackson
*Assistant Examiner* — Marie Archer
(74) *Attorney, Agent, or Firm* — Tarolli, Sundheim, Covell & Tummino LLP

(57) ABSTRACT

A modular system for acquiring biometric data includes a plurality of data acquisition modules configured to sample biometric data from at least one respective input channel at a data acquisition rate. A representation of the sampled biometric data is stored in memory of each of the plurality of data acquisition modules. A central control system is in communication with each of the plurality of data acquisition modules through a bus. The central control system is configured to collect data asynchronously, via the bus, from the memory of the plurality of data acquisition modules according to a relative fullness of the memory of the plurality of data acquisition modules.

17 Claims, 7 Drawing Sheets

(56) References Cited

U.S. PATENT DOCUMENTS

| | | | |
|---|---|---|---|
| 4,053,951 A * | 10/1977 | Hudspeth et al. | 600/301 |
| 4,138,732 A * | 2/1979 | Suzuki et al. | 710/31 |
| 4,145,755 A * | 3/1979 | Suzuki et al. | 710/57 |
| 4,847,812 A * | 7/1989 | Lodhi | 365/221 |
| 4,909,260 A * | 3/1990 | Salem et al. | 600/534 |
| 4,995,005 A * | 2/1991 | Lodhi | 365/221 |
| 5,348,008 A | 9/1994 | Bornn et al. | |
| 5,353,248 A * | 10/1994 | Gupta | 365/154 |
| 5,464,012 A | 11/1995 | Falcone | |
| 5,724,580 A | 3/1998 | Levin | |
| 5,832,448 A | 11/1998 | Brown | |
| 5,857,967 A | 1/1999 | Frid et al. | |
| 5,898,893 A * | 4/1999 | Alfke | 710/57 |
| 5,899,855 A | 5/1999 | Brown | |
| 5,966,692 A | 10/1999 | Langer et al. | |
| 6,157,989 A | 12/2000 | Collins et al. | |
| 6,161,095 A | 12/2000 | Brown | |
| 6,166,673 A * | 12/2000 | Odom | 341/155 |
| 6,168,563 B1 | 1/2001 | Brown | |
| 6,213,942 B1 | 4/2001 | Flach et al. | |
| 6,221,012 B1 | 4/2001 | Maschke et al. | |
| 6,290,646 B1 | 9/2001 | Cosentino et al. | |
| 6,339,558 B1 * | 1/2002 | Ioki | 365/221 |
| 6,405,269 B1 * | 6/2002 | Camilleri et al. | 710/57 |
| 6,482,156 B2 | 11/2002 | Iliff | |
| 6,485,418 B2 | 11/2002 | Yasushi et al. | |
| 6,503,206 B1 | 1/2003 | Li et al. | |
| 6,532,434 B1 * | 3/2003 | West | 702/187 |
| 6,579,231 B1 | 6/2003 | Phipps | |
| 6,612,985 B2 | 9/2003 | Eiffert et al. | |
| 6,615,067 B2 | 9/2003 | Hoek et al. | |
| 6,648,820 B1 | 11/2003 | Sarel | |
| 6,697,765 B2 | 2/2004 | Kuth | |
| 6,720,887 B1 | 4/2004 | Zunti | |
| 6,730,025 B1 | 5/2004 | Platt | |
| 6,735,551 B2 | 5/2004 | Voegeli et al. | |
| 6,740,033 B1 | 5/2004 | Olejniczak et al. | |
| 6,773,397 B2 | 8/2004 | Kelly | |
| 6,781,067 B2 | 8/2004 | Montagnino et al. | |
| 6,820,057 B1 | 11/2004 | Loch et al. | |
| 6,958,705 B2 | 10/2005 | Lebel et al. | |
| 6,970,827 B2 | 11/2005 | Zeltzer et al. | |
| 7,129,836 B2 | 10/2006 | Lawson et al. | |
| 7,223,235 B2 | 5/2007 | Brown | |
| 7,252,636 B2 | 8/2007 | Brown | |
| 7,258,666 B2 | 8/2007 | Brown | |
| 7,292,139 B2 | 11/2007 | Mazar et al. | |
| 7,310,668 B2 | 12/2007 | Brown | |
| 7,320,030 B2 | 1/2008 | Brown | |
| 7,321,862 B2 | 1/2008 | Rosenfeld et al. | |
| 7,353,179 B2 | 4/2008 | Ott et al. | |
| 7,356,478 B1 | 4/2008 | Kohli | |
| 7,366,285 B2 | 4/2008 | Parolkar et al. | |
| 7,382,247 B2 | 6/2008 | Welch et al. | |
| 7,387,607 B2 | 6/2008 | Holt et al. | |
| 7,390,299 B2 | 6/2008 | Weiner et al. | |
| 7,618,260 B2 * | 11/2009 | Daniel et al. | 439/37 |
| 2003/0053367 A1 * | 3/2003 | Condorelli et al. | 365/239 |
| 2003/0177295 A1 * | 9/2003 | Hsu et al. | 710/200 |
| 2003/0181795 A1 * | 9/2003 | Suzuki et al. | 600/300 |
| 2005/0044327 A1 * | 2/2005 | Howard et al. | 711/147 |
| 2005/0054941 A1 * | 3/2005 | Ting et al. | 600/529 |
| 2006/0031487 A1 | 2/2006 | Noguchi et al. | |
| 2006/0252999 A1 * | 11/2006 | Devaul et al. | 600/300 |
| 2007/0073266 A1 | 3/2007 | Chmiel et al. | |
| 2008/0046627 A1 * | 2/2008 | Castro et al. | 710/313 |
| 2009/0055677 A1 * | 2/2009 | Chen | 713/600 |

OTHER PUBLICATIONS

Tanielian, M. H. et al, in "Pressure Belt: An integrated Multisensor System", IEEE, 2002, p. 1182-1187.*

International Search Report—2 pgs. Dated Apr. 29, 2009, ZIN Technologies, Inc.

Written Opinion—5 pgs. Dated Apr. 29, 2009, ZIN Technologies, Inc,

* cited by examiner

DATA ACQUISITION FOR MODULAR BIOMETRIC MONITORING SYSTEM

GOVERNMENT INTEREST

The subject innovation is being developed with government support under Contract No. NNC05CA65C awarded by NASA. The United States government may have certain rights in the invention.

RELATED APPLICATION

This application relates to U.S. patent application Ser. No. 11/236,899, which was filed on Sep. 28, 2005, and entitled COMPACT WIRELESS BIOMETRIC MONITORING AND REAL TIME PROCESSING SYSTEM, the entire contents of which application is incorporated herein by reference.

BACKGROUND

Diagnosis of ailments and treatment of disease often requires an analysis of biological signs obtained from a patient in the course of normal activity over a period of time. Personal health monitors are commonly employed to gather data related to a patients biometric data.

In general, a personal health monitor is a device used to measure and record one or more clinical parameters of a patient for later transmission to the patient's physician or other health care provider. The personal health monitor may be used in a hospital or clinical setting as an adjunct to existing care. Additionally, the personal health monitor may also be used by the patient outside care facilities (e.g., at a patient's home). When used by a patient at home, the patient operates the personal health monitor to record certain bodily clinical parameters. The personal health monitor can be used by the patient who has a condition requiring monitoring of one or more clinical parameters, but who otherwise may not require the level of care such as provided by a hospital. Accordingly, the personal health monitor provides potential savings in medical costs involved with a hospital stay.

For example, continuously monitoring cardiac patients immediately following coronary attacks is important. Such is normally accomplished effectively in the coronary care unit of most hospitals where the patients are continuously monitored following heart attacks to detect arrhythmias of the heart, for example monitoring and warning for ventricular arrhythmias, which may lead to ventricular fibrillation and death. Through prompt recognition and treatment of such warnings related to ventricular arrhythmias in coronary care units, the mortality rate of acute myocardial infarctions has been reduced considerably. In addition, many post myocardial infarction cardiac patients continue have frequent ventricular extra systoles after discharge from the hospital. Accordingly, it is desired to continuously monitor the patient over a certain period of time and under varying conditions of stress, to determine the effectiveness treatment which has been introduced, such as the proper dosage of medication.

Constant monitoring of such patients after release from the hospital may be difficult because of the logistics involved, and particularly since they can no longer be monitored closely as a group by direct wiring or close telemetry, as commonly implemented in hospital settings. As a result, various systems have been developed to attempt to monitor the ECG signals of out-patients to thereby provide a diagnostic tool for additional treatment or variation of treatment for the patients as may be required.

Nevertheless, many such mobile units are typically spacious and difficult to set up and maintain. Moreover, in general these units are not suitable for readily monitoring a plurality of biological conditions and indicators useful for many situations. In addition, such systems lack flexibility during usage as they typically have fixed sensor types and configurations.

SUMMARY

The invention relates to systems and methods for collecting data from a plurality of data acquisition modules. For example, the approach described herein enables data to be acquired at one or more modules synchronously and to be collected from such module(s) by a central control asynchronously, such as based on relative fullness of memory at the one or more modules.

One aspect of the invention relates to a modular system for acquiring biometric data. The system includes a plurality of data acquisition modules configured to sample biometric data from at least one respective input channel at a data acquisition rate. A representation of the sampled biometric data is stored in memory of each of the plurality of data acquisition modules. A central control system is in communication with each of the plurality of data acquisition modules through a bus. The central control system is configured to collect data asynchronously, via the bus, from the memory of the plurality of data acquisition modules according to a relative fullness of the memory of the plurality of data acquisition modules.

Another aspect of the invention relates to a biometric monitoring system that includes a plurality of modular components configured to sample biometric data received from at least one respective input channel according to a data acquisition rate. Each of the plurality of modular components includes a first memory structure for storing housekeeping information associated with operation of the modular component. Each of the plurality of modular components also includes a second memory structure for storing a representation of the sampled biometric data. The housekeeping information in the first memory structure is updated in response to storing the representation of the sampled biometric data in the second memory structure. A master module is configured to retrieve data asynchronously, via a bus to which each of the plurality modular components is connected, from the second memory of the plurality modular components according to a relative fullness of the second memory structure in each of the plurality modular components as determined by the master module based on the updated housekeeping information in the plurality of modular components.

Still another aspect of the invention relates to a method for acquiring biometric data. The method includes sampling biometric data for each of the plurality of modular components at a substantially synchronous data acquisition rate and storing the sampled biometric data in a first memory structure of each of the respective plurality of modular components. A counter in a second memory structure of each of the plurality of modular components is updated in response to the storing of the sampled biometric data. A fullness of the first memory structure in each of the plurality of modular components is determined based at least in part on the updated counter in the second memory structure of each respective modular component and biometric data is retrieved from at least one of the plurality of modular components in response to the determined fullness of the first memory structure in the at least one of the plurality of modular components.

DETAILED DESCRIPTION

The subject innovation relates to systems and methods to perform data acquisition in a modular system. For example, the approach described herein enables data to be acquired at one or more modules synchronously and to be collected from such module(s) by a central control asynchronously, such as based on relative fullness of memory at the one or more modules.

Figure 1:
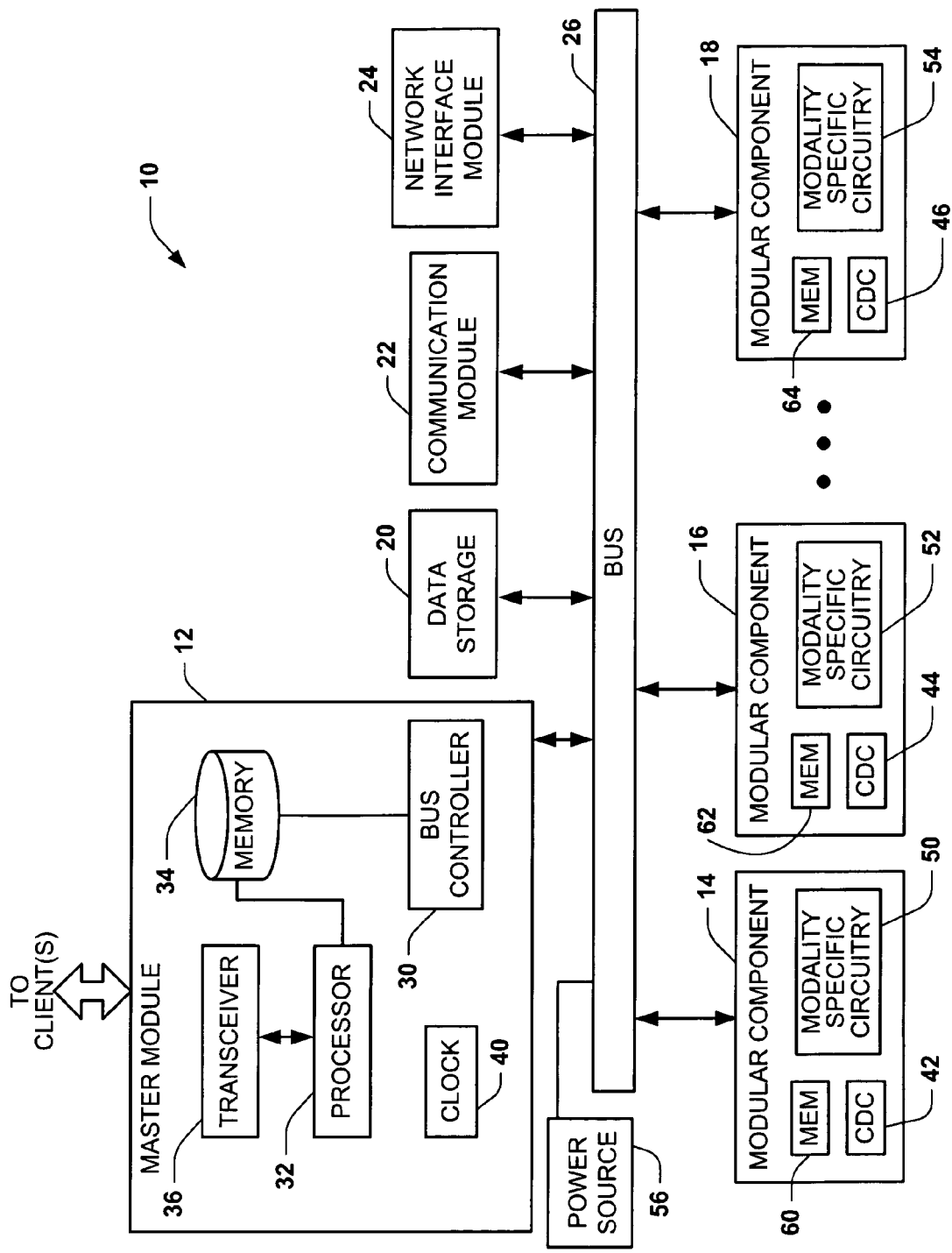
FIG. 1 depicts an example of a biometric monitoring system that can be implemented according to an aspect of the invention.

FIG. 1 depicts an example of a system 10 that can be utilized to acquire biometric data. As used herein, the term "biometric data" or related phrases (e.g., "biometric parameter" and "biometric information") is intended to encompass biological or biomedical information, such as may be acquired from one or more sensors. Biometric data can also relate to information associated with controlling or monitoring the delivery of a therapy being delivered to a patient or it can also represent information associated with controlling drug delivery equipment or sensor equipment or operating parameters associated with sensor status and operation that may be employed in connection with the acquisition of data or control of therapy devices.

The system 10 includes a plurality of modules, which are also referred to herein as modular components. In the example of FIG. 1, the system 10 includes a master module 12 and a plurality of other modular components 14, 16, 18, 20, 22 and 24. Each of the respective modular components 12-24 can be programmed and/or configured according to the intended use of the system 10. At least some of modular components 14, 16, 18, 20, 22 and 24 can be replaced, inserted and/or swapped to achieve a desired aggregate function, such as can include collection of biometric parameters, control delivery of a desired therapy, communication of data to and from the system 10 or any combination thereof.

For example, a clinician can determine a customized routine for acquisition of biometric data and or therapy. Based on the routine, the clinician can determine which types of modules should be inserted into the system as the modular components 12-24. For instance, the modular components 14 and 16 can be configured to acquire biometric data associated with a patient and the modular component 18 can deliver a desired type of therapy (e.g., electrical and/or chemical) to a patient.

By way of further example, the modular component 14 can measure one or more biometric parameters, and/or supply input that is representative of the status of a controlled process. The input can be provided to the master module 12 or another modular component 18, such as can be configured to change one or more outputs for effecting control of the therapy process. For instance, one or more of the modular components 12, 14 and 16 can supply activation commands to a glucose pump in a patient's proximity, such as when acquired data that pertains to blood sugar of a patient indicates a critical level. Similarly, muscle tension can be employed as a biometric condition to be collected by a modular component, and employed for delivery of chemical or electrical therapy to perform muscle relaxation by the same or a different modular component to a patient. The inputs and outputs of each of the modular component 12-24 can be binary, (e.g., on or off), and/or analog assuming a continuous range of values.

Each of the respective modular components 12-24 can communicate over a data bus or backplane 26. For example, the bus 26 can enable communication between the master module 12 and any of the other modular components 14-24. Additionally or alternatively, each of the modules 12-24 can communicate with each other over the bus 26. Those skilled in the art will understand and appreciate various types of buses or communication links and communications protocols that can be utilized to provide for communication between the respective modules 12-24.

As a further example, each of the modular components 14-24 can be connected to the bus via a physical interface (e.g., a slot having a given form factor) having a predetermined physical address location in communication with the bus 26. The master module 12 can thus communicate with each module using this physical address, such as part of a configuration mode in which the master module 12 acquires information (e.g., hardware configuration) about each modular component 14-24 that is connected to the bus 26. The master module 12 can also assign each other modular component 14-24 a respective address that can be utilized to facilitate subsequent communication with the modular components over the bus 26, such as for sending requests and responses during normal operation.

The system 10 can be considered a distributed computing arrangement since certain processing functions can be distributed to the respective modules 14-24. In this way, computing power requirements of the master module 12 can be reduced based upon the portions of processing being implemented at the respective components 14-24. In this respect, the power usage of the system 10 can be scaled to the medically desired configuration of the system. By way of further example, each of the modules 14, 16 and 18 can correspond to a modular apparatus that can be utilized to acquire biometric data that can be transmitted to the master module 12 for aggregate communication to one or more remote clients, such as a Personal Digital Assistant (PDA), computer, workstation, a server and the like.

In the example of FIG. 1, the master module 12 can include a bus controller 30 that can be utilized to control data communication over the bus 26. For instance, the bus controller 30 can transmit data (e.g., in the form of data requests) from the master module 12 to the respective modular components 14 through 24 via the bus 26, such as mentioned above. As one example, the master module 12 can provide respective program instructions to one or more of the modules 14 through 24 for controlling operation and the particular function being performed by the respective module(s). This can include setting one or more operating parameters sampling rates, configuration settings as well as defining the specific functions or tasks being performed by the respective components. The bus controller 30 can also be configured to control how and when each of the respective modules communicates data over the bus 26.

The master module 12 also includes a processor 32 that can execute program instructions stored in associated memory 34. The memory 34 can be implemented as including one or more different types of memory, such as volatile or nonvolatile memory. The memory 34 can be accessed by the processor 32 for storing executable instructions for controlling operation of the master module 12 and the system 10, more generally. The memory 34 can also be utilized to store data that is provided to the master module via the transceiver 36 or bus controller 30. For example, the memory 34 can be employed as a temporary data storage device for biometric data and control information that may be received from any of the other respective modules 14 through 24 via the bus 26.

According to one aspect of the invention, the memory 34 can store executable instructions that control high level functions of the bus controller 30 to facilitate and optimize traffic over the bus 26. For example, the processor 32 can control the bus controller 30 to collect data from each of the respective modules 14-18 asynchronously according to a relative fullness of memory in each of the respective modules. The master module 12 can determine the relative fullness of the modules in response to requesting certain housekeeping information from the modules. For instance, certain housekeeping information (e.g., corresponding to the type of module, sampling rate, memory storage capacity) can be obtained by the master module 12 during a configuration or set-up mode. The master module can employ the bus controller to request status information (e.g., intermittently or periodically) from the respective modules, which status information can be utilized in conjunction with the previously acquired housekeeping information to determine a relative fullness of the memory in each module. For example, a process running in the processor 32 can cause the bus controller to issue requests for data from one or more of the modular components 14, 16, and 18 based on the determined fullness of memory at each of the respective modules. In this way the master module 12 can acquire data from modules at different rates to reduce traffic on the bus 26. The relative fullness thus may vary according to the particular functions each module is performing, the rate data is sampled and stored and the capacity of the memory for storing such data at each module.

The processor 32 can also control other functions associated with the system 10 such as communication to one or more clients through the respective transceiver 36. The transceiver 36 can be implemented as a wired or wireless type of communication device. Those skilled in the art will understand and appreciate various types of transceivers that can be utilized by the master module 12 to transmit and/or receive data. For instance, the processor 32 can transfer data from the memory 34 to the associated client via the transceiver 36. Alternatively, the client may be configured to access and download data from selected portions of the memory 34. For example, the client can run an appropriate user interface (not shown) to initiate or terminate or otherwise control one or more functions associated with operation of the system 10. The transceiver 36 further can be utilized for programming operation of the system 10 through an appropriate input/output port.

The master module 12 can also include a clock 40 that is used to control timing associated with operation of the master module 12 as well as to control the timing associated with data transfers over the bus 26 via the bus controller 30. The master module 12 can also employ the clock 40 to control internal operation of the master module, including communication via the transceiver 36.

The system 10 can further include a data storage module 20 that can be utilized for storing additional data that is transmitted over the bus 26. For example, the processor 32 can store data to the data storage module 20. Additionally or alternatively, the data storage module 20 can be implemented as a modular component similar to the other modules 12-18, 22 and 24 in the system 10. For example, a module having a desired memory capacity can be connected to the bus as the data storage module 20 to increase the overall storage capacity of the system 10. This would allow the data storage function of one or more of the other the modular components 12-18, 22 and 24 to be distributed to the data storage module, further increasing the cost efficiency associated with such modules since such modules can be configured with reduced memory requirements. A client thus may be able to access and retrieve data from the data storage module 20 via the master module (through the transceiver 36, processor 32 and bus controller 30) and bus 26.

The client may also communicate with the data storage module 20 or other modules 12-18, 22 and 24 in the system 10 by other communication devices. For example, the system 10 can include addition means of communicating to one or more external devices, such as a communication module 22. For example, the communication module 22 can correspond to a wireless communication module. The communication module 22, for example, can transmit according to any one of a variety of known wireless protocols, such as an 802.11x standard (e.g., WiFi), 802.16x standard (e.g., WiMAX), Bluetooth, cellular communications (e.g., GSM, UMTS and PCS) and the like.

Additionally or alternatively, the system 10 can include a network interface module 24 that can be programmed and/or configured to connect to a computer network, such as a local area network (LAN) or a wide area network (WAN) such as including the internet. As one example, the network interface module 24 can be electrically connected to the network via a standard network connection. The network interface module 24 thus can provide an appropriate connection with the desired network. Thus, in the example of FIG. 1, communications can be implemented over the bus 26 via the bus controller 30, over the bus through the network interface module 24 and over the bus via the communication module 22. In this way data can be transmitted to and received from the system 10 via the network interface module 24.

In the example of FIG. 1, the modular components 14, 16 and 18 can be programmed and/or configured based on the requirements of the biometric condition(s) that is to be measured and/or other functions that are to be controlled, such as including the administration of a desired therapy. Each of the respective components 14, 16 and 18 can includes a common architecture, which corresponds to circuitry referred to herein as being embodied in a common data controller (CDC) 42, 44 and 46. As one example, each of the CDCs 42, 44 and 46 can be a common architecture that includes a processor or controller and other circuitry that is programmed and configured to control operation of the modular component as well as to facilitate communication to and from the respective modular component via the bus 26.

Each of the modular components 14, 16 and 18 also includes modality specific circuitry 50, 52 and 54. The modality specific circuitry can vary according to the type of biometric condition data that is to be acquired by a respective module and/or the type of therapy that might be delivered by the respective module. That is, the modality specific circuitry 50, 52 and 54 of each of the modules 14, 16 and 18 is programmed and/or configured to perform a predetermined biometric function (e.g., sensing or therapeutic function—a/k/a modality). For instance, one or more of the modules 14, 16 and 18 can be configured to acquire a predetermined type of biometric condition data by sensing biometric or biological conditions of a patient. Thus, each modular component 14, 16 and 18 can include a particular number of channels for acquiring biometric data from one or more sensors that can be arranged to detect corresponding biometric or biological conditions.

By way of further example, each of the modality specific circuitry 50, 52 and 54 can be adapted to acquire data related to the modalities of electromyography (EMG), electrocardiography (ECG), electroencephalography (EEG), plantar pressure, joint angle, pulse oximetry, blood pressure, core body temperature, blood glucose, and the like. Additionally or alternatively, one or more other modules 14, 16 and 18 can be configured to administer a desired therapy (e.g., electrical or chemical therapies) via corresponding delivery mechanisms.

Thus, each of the modality specific circuitry 50, 52, and 54 includes circuitry operative to provide one or more input signal indicative of a biometric condition. As mentioned above, the input signals can be received by the CDC 42, 44, and 46 over a set of channels that can be configured according to the particular modality. The signal for each channel further can be filtered and processed by the modality specific circuitry 50, 52 and 54 to provide a digital representation of such signal, each of which individually or collectively corresponds to a sensed biometric condition of the patient. Alternatively, in other circumstances, the modality specific circuitry 50, 52 and 54 can provide a signal (e.g., feedback signal) associated with a delivery of a therapy to the patient, such as may be in the form of chemical or electrical therapies.

Each modular component 14, 16, 18 further can be programmed to sample the input signal(s) for synchronously acquiring biometric data at a data acquisition rate. Sampling of the input signal can be performed in the analog or digital domain. The data acquisition rate can be set via the CDC or the modality specific circuitry of a respective modular component. According to one embodiment, each modular component 14, 16, 18 can sample a digital representation of the input signal at a respective data acquisition rate. The data acquisition rate for a given modular component 14, 16, 18 can be fixed or it can be variable, such as may vary depending on the operating mode (or state) of the given modular component or the particular monitoring function being performed. The sampled biometric data can be stored in corresponding memory 60, 62 and 64 of each modular component 14, 16 and 18. When the biometric data is stored, a counter (or an index) can be incremented in the memory 60, 62 and 64. The counter thus may store an indicator value commensurate with the amount of memory (e.g., bits or bytes or other units of memory) or location in memory that has been written with biometric data.

The master module 12 can retrieve the counter value from one or more of the modular components 14, 16 and 18. Since the amount of memory in each modular component is known by the master module 12 (e.g., by housekeeping information retrieved from the modular component), the master module further can control retrieval of the biometric data from each modular component 14, 16 and 18 based on the indication of memory fullness determined for each respective modular component from the counter value. Additionally, or alternatively, the master module 12 can determine or estimate a rate at which the memory is being filled to further assist in coordinating retrieval of the biometric data from the modular components 14, 16 and 18. For example, the master module 12 can determine a change in the counter value for a given modular component over time (e.g., from a comparison of a preceding counter value of the counter relative to a subsequent counter value after a plurality of clock cycles or since a last retrieval of the counter value). The master module 12 can also obtain an indication of the sample rate and an indication of the number active channels to provide a basis for controlling retrieval of data from the modular components 14, 16 and 18. Those skilled in the art thus will appreciate that the bus controller 30 and instructions executed by the processor 32 in the master module 12 can operate as means for controlling retrieval of data from the modular components 14, 16 and 18.

As mentioned above, each of the modular components 12-24 can have a form factor, which may be a standard or proprietary form factor, which is dimensioned and configured for swappable connection into the system 10. Thus, as the intended use of the system changes, different modular components can be replaced or swapped for other modules so that the aggregate system meets the needs for particular patient. The amount of memory for storing biometric data can further vary depending on the intended function of a given module. The master module 12 thus can retrieve data from a given modular component based on the relative fullness determined by the master module for the modular component' memory, such as based on the known configuration and the counter value for the respective modular component. The particular combination of data acquisition and/or therapy administration thus can be tailored on a patient-by-patient basis by interchanging or swapping various modular components, having different modality specific circuitry, into or out of the system 10.

Additionally, the respective connections between the modules 12-24 and the bus are schematically represented as bi-directional arrows. Such connections enable data communication from a given one of the respective modules to one or more other modules over the bus 26, such as under the control of the bus controller 30 in the master module 12. Additionally, the connections can provide power to each of the respective modules 12-24. For instance, a power source 56, such as including a voltage regulator and one or more batteries) can distribute power to each of the respective modules via the bus 26 or other power distribution means. Alternative power systems can be utilized to provide power, such as may be implemented by separate power connections or in one or more of modules 12-24.

Figure 2:
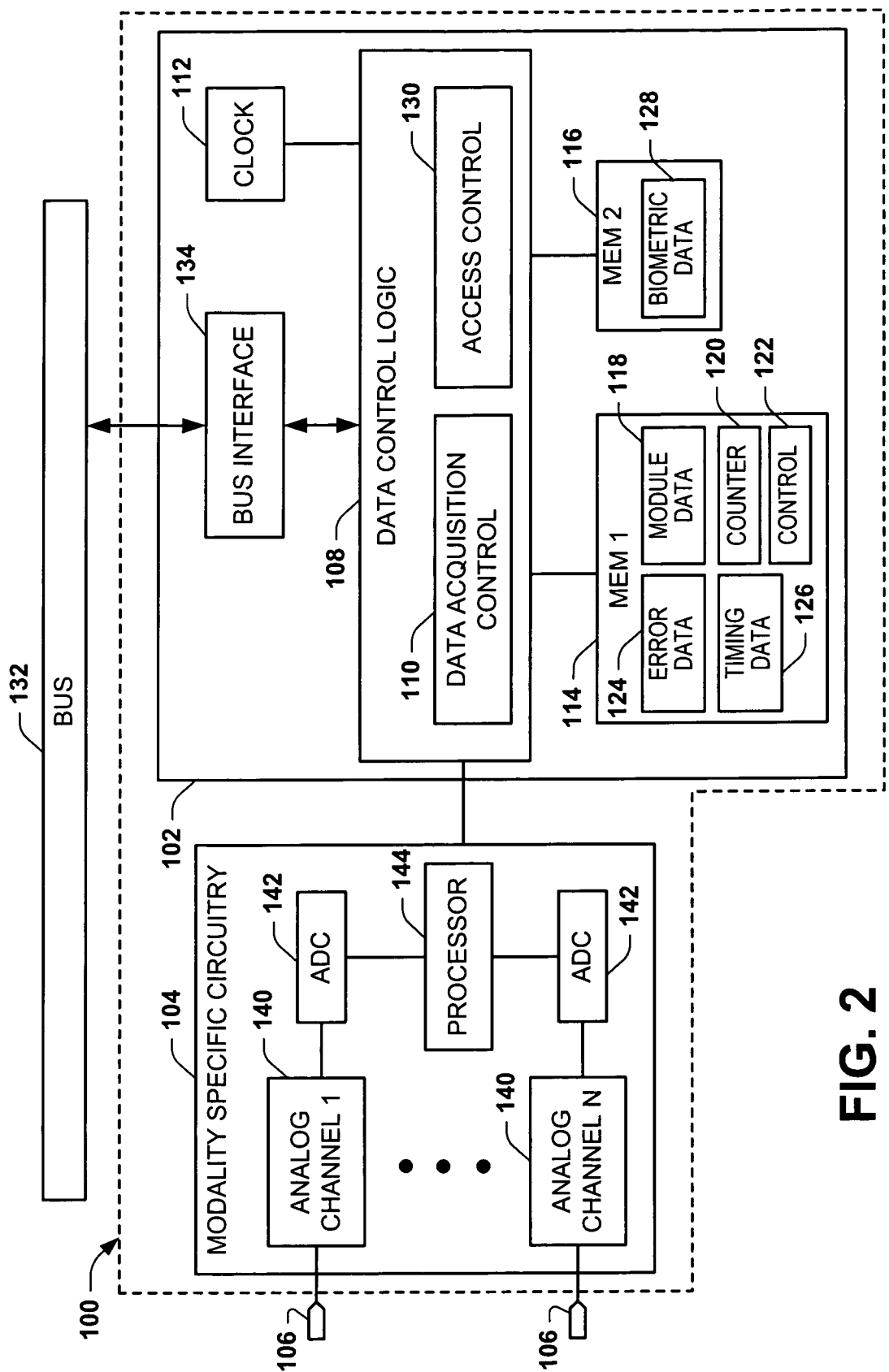
FIG. 2 depicts an example of a modular component that can be implemented in a biometric monitoring system according to an aspect of the invention.

FIG. 2 depicts an example of a modular component 100 that can be implemented according to an aspect of the invention. The modular component 100 includes a CDC 102 that is electrically coupled with modality specific circuitry 104. The modular component 100 can be self contained within a module housing having a preconfigured form factor, which can vary according to system requirements, such as including but not limited to the examples shown and described herein. The modality specific circuitry 104 includes one or more inputs or outputs, indicated at 106, that can be electrically coupled to respective sensors or therapy delivery devices (not shown). While for purposes of simplification of explanation a single modular component is depicted in FIG. 2, those skilled the art will understand and appreciate that a system can include any number or one or more modular component based on the teachings contained herein.

In the example of FIG. 2, the CDC 102 includes data control logic 108 that is programmed and configured to control data storage and retrieval for the modular component 100. For example, the data control logic 108 can include data acquisition control 110 that is programmed to control the data acquisition rate at which input signals from the modality specific circuitry 104 are sampled. For instance, the data acquisition control 110 can implement a sampling rate based on the type of modular component and its intended purpose, as well as based on a current operating mode. The sampling rate may also vary (e.g., it may be increased or decreased) in response to a biometric condition that is detected by the modality specific circuitry 104, in response to a condition detected by one or more other module or in response to control instructions from a master module (not shown). The data acquisition control 110 can control the sampling rate based on a clock signal provided by a clock 112. For instance, the data acquisition control 108 can employ a timer, counter or other time basis to periodically sample the input data from the modality specific circuitry 104 at the defined rate. While the data acquisition control 110 is depicted as being implemented in the CDC 102, such functionality could be performed by the modality specific circuitry 104 or through cooperation by both the CDC and the modality specific circuitry.

The CDC 102 also includes memory for storing data and executable instructions. In the example of FIG. 2, the memory includes a first memory structure 114 and a second memory structure 116. Each memory structure 114 and 116 can be implemented as non-volatile memory, volatile memory or a combination of different memory devices that is configured for storing data and executable instructions. The memory structures 114 and 116 can be different physical memory devices or they may correspond to separate blocks of memory allocated within a common memory device.

In the example of FIG. 2, the first memory structure 114 stores housekeeping data (e.g., data associated with the module's configuration and operation) and executable instructions for the modular component 100. Such housekeeping information can be utilized to determine the health or status of the modular component 100, such as by the master module (not shown). As one example, the first memory structure 114 can store module data 118, counter data 120, control data 122, error data 124 and timing data 126. The module data 118 can include module identification information (e.g., model number, serial number and the like). The module data 118 thus can be utilized (by the master module) to ascertain the intended purpose or function and operating parameters of the modular component 100. The control data 122 can include instructions and data that define functions and parameters of the data control logic 108. The error data 124 may include information that identifies operating errors for the CDC 102 and/or modality specific circuitry 104, such as error flags, calibration errors, and timing errors to name a few. The timing data 126 can be utilized to store timing information associated with various aspects of operation of the CDC 102, including speed of the clock 112, a local relative time base (e.g., as may be measured from start-up or other predetermined events).

The second memory structure 116 stores biometric data 128 that is sampled from the modality specific circuitry 104. The counter data 120 of the first memory structure 114 has a value that is indicative of an amount of the biometric data 128 that is stored in the second memory structure 116. For example, the data in the counter 120 can correspond to an incremental count of the units of memory (e.g., bits or bytes) that are written to in the second memory structure 116. Alternatively or additionally, the counter data 120 can define a location or offset of the data that is written into the second memory structure 116. For instance, the counter data 120 can be utilized as an index (or indices) that define a block (or blocks) of biometric data stored in the memory structure 114. Such an index can be utilized to address corresponding memory locations in the second memory structure 116 for retrieving the biometric data 128. Errors associated with the biometric data 128 can be retrieved from the other memory structure 114, such as corresponding to the error data 124. Such errors can be utilized, for example, to diagnose and/or to repair malfunctioning circuitry and software at the modular component 100, such as by program instructions running on the master module or another modular component.

The data control logic 108 may also be programmed and configured to perform an access control function 130 (which may include separate access control functions) for accessing each of the respective memory structures 114 and 116. The access control function 130 can also update the counter data 120 in response to biometric data being stored in the second memory structure 116. The second memory structure 116 can be implemented as a FIFO data structure, such that a single address or index value can be utilized to define the biometric data 128 stored in such memory. For instance, the access control function 130 can increment the counter 120 by an amount commensurate with the amount of biometric data that is stored in the second memory structure 116. The access control function 130 can thus employ the counter data 120 (or other control instructions) as an index for accessing and retrieving the biometric data 128 from the second memory structure 116.

As a further example, a master module or another modular component (or process running in the system) that is in communication with the modular component 100 through a bus 132 can transmit a request to the modular component. The request, for instance, can be a request for data from the first memory structure 114, such as may include any of the data stored therein, individually or in combination. The request can be provided to the data control logic 108 via a bus interface 134. In response to the request, the data control logic 108 employs the access control function 130 to retrieve the requested data from the first memory structure 114, which in this example includes at least the counter data 120. The access control function 130 thus can provide a response, including the requested information, to the requesting module via the bus interface 134. The requesting module can also issue a subsequent request for biometric data from the modular component 100, which again is received by the bus interface 134 and processed by the data control logic 108. The request can include a counter value or other address location that is utilized by the access control function 130 to locate the requested biometric data from the second memory structure 116. The counter value or other location information can be derived from the information sent in a prior response, such as from the module 100 to a master module. The access control function 130 in turn provides a set of one or more responses that includes the requested biometric data 128.

The bus interface 134 coordinates the sending of the response data over the bus 132 back to the requesting module. Additionally, after retrieving the requested data from the second memory structure 116, the access control function 130 can reset the counter data 120 to its appropriate starting value, which starting value can indicate the absence of biometric data remaining in the second memory structure 116. It will be appreciated that the master module or other requester can request less than all the biometric data 128 from the second memory structure 116, such as by specifying an offset or location that does not encompass all such biometric data. After the portion of requested biometric data is retrieved from the memory structure 116, the access control function 130 can set the counter 120 to an appropriate value to indicate an offset or location for the remaining biometric data 128 in such memory.

The modality specific circuitry 104 includes corresponding analog circuitry 140 depicted as an analog channel 1 to analog channel N, where N is a positive integer denoting the number of available channels for sending or receiving information and commands. Each analog channel 140 is associated with a respective I/O port 106, such as for providing isolation and analog pre-processing the respective input signal. While the modality specific circuitry 104 may have N available channels, it is to be understood that not every channel needs to be an active channel. The particular number of active channels 140 can be set in the module data 118 and or the control data 122 in the CDC 102. Those skilled in the art will understand and appreciate various types of circuitry (e.g., isolation amplifiers, filters, gain scaling circuits and the like) that can be utilized to receive and process signals from appropriate sensors and provide corresponding input signals for each channel. The particular circuitry that forms each respective channel 140 and how it may be configured in the modality specific circuitry 104 thus can vary according to the modality and the biometric conditions intended to be monitored by the modular apparatus 100. Alternatively, the analog channels 140 might correspond to output or control circuitry (e.g., drivers and logic) configured to control delivery of appropriate therapies, such as a chemical or electrical based therapies. The analog channels 140 further can provide for isolation between the leads and sensors connected at the ports 106 and the other processing performed by the modality specific circuitry 104.

Each active analog channel 140 can provide an analog input signal to an analog-to-digital converter (ADC) 142 that provides corresponding digital channel representation. The ADC 142 provides the digital channel representation to a processor (e.g., digital signal processor) 144 that can be programmed to perform additional signal processing on each digital channel representation. The processor 144 can provide the processed data to the CDC 102, which can be sampled by the data acquisition control 110 according to a defined sample rate, such as described above.

Figure 3:
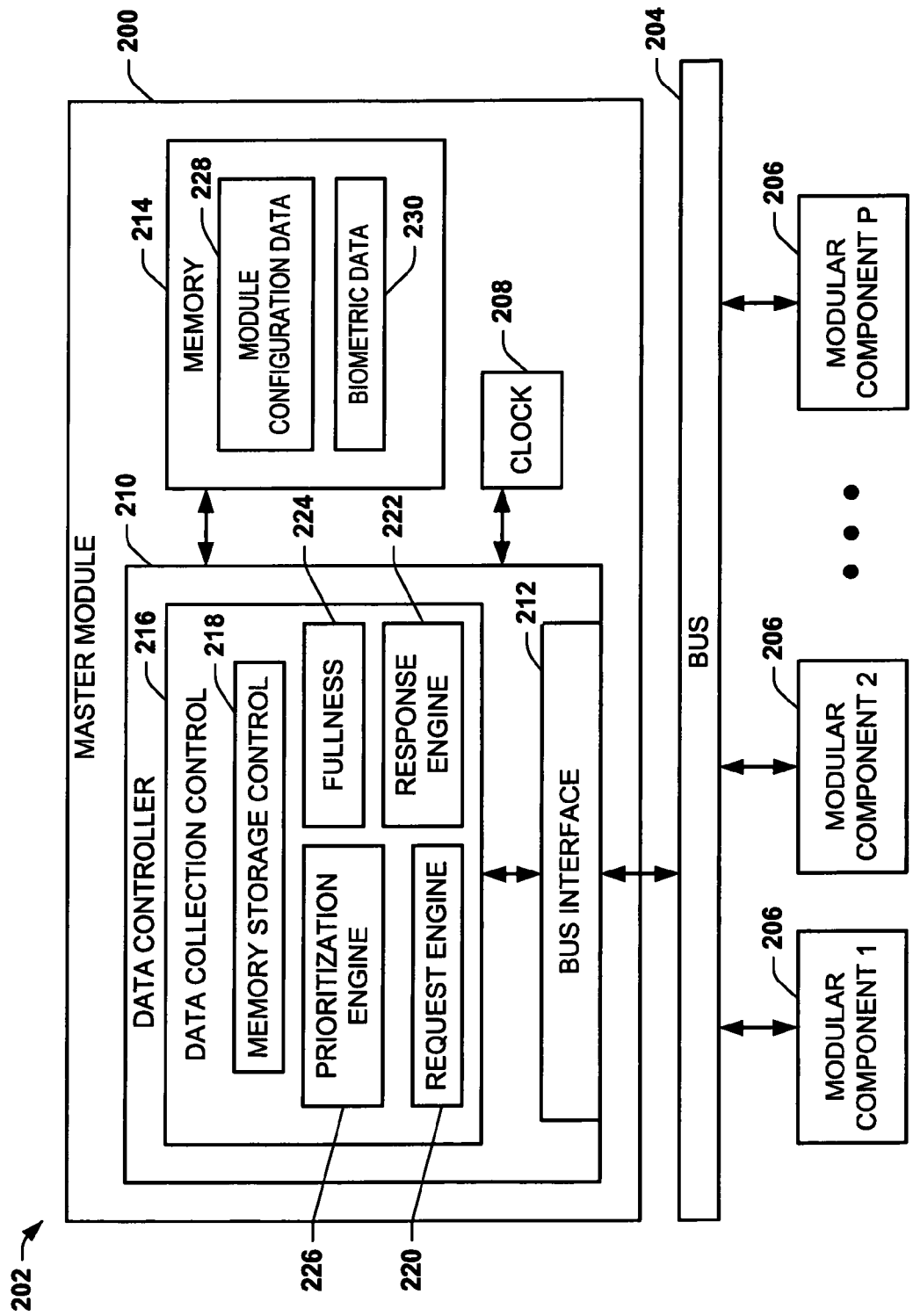
FIG. 3 depicts an example of a master module that can be implemented in a biometric monitoring system according to an aspect of the invention.
Figure 4:
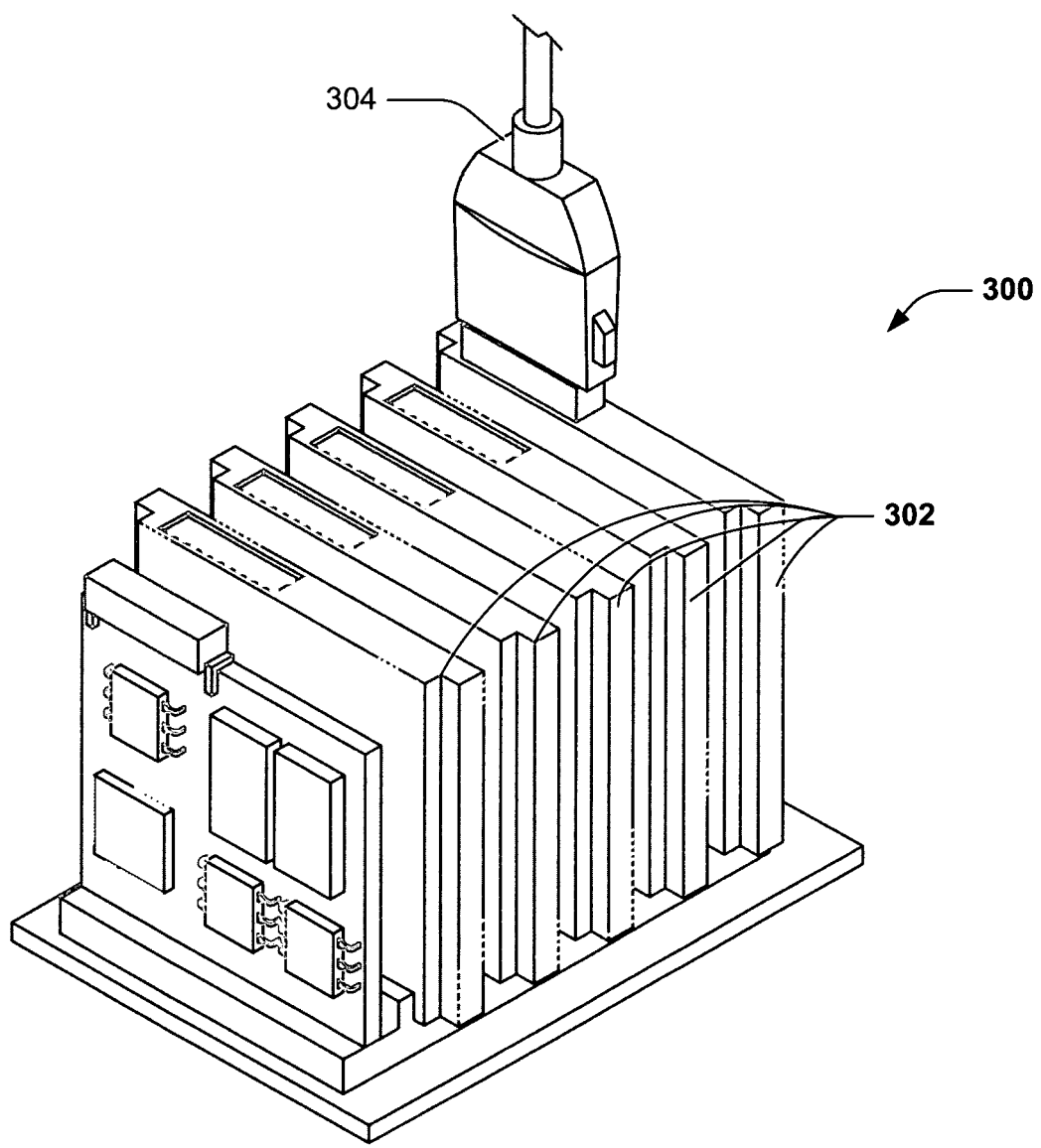
FIG. 4 depicts an example of a modular system that can be implemented according to an aspect of the present invention.

FIG. 3 depicts a functional block diagram of a master module 200 that can be implemented in a biometric monitoring system 202 according to an aspect of the invention. The biometric monitoring system 202 thus can include a data bus 204 over which communication between the master module 200 and one or more modular components 206 can occur. In the example of FIG. 4, the modular components 206 are indicated at modular component 1, modular component 2 through modular component P, where P is a positive integer denoting the number of modular components in the system 202. At least a substantial portion of the modular components 206 can include modality specific circuitry that can be programmed and configured for monitoring a desired biometric condition as well as for delivering a therapy to a patient such as described herein.

In the example of FIG. 3, the master module 200 includes a data controller 210 that can be programmed and configured to control access and retrieval of data within the system 202. For instance, the data controller 210 can be implemented as computer executable instructions running in a processor for controlling other circuitry including a bus interface 212 for sending and receiving requests and responses over the bus 204. The data controller further can control access to associated memory 214 that can reside in the master module 200. The memory 214 can be implemented as volatile or non volatile memory that can include the executable instructions for controlling operation of the master module as well as for storing data retrieved from one or more of the other modules 206. It is to be understood and appreciated that while the memory 214 is depicted as residing within the master module 200, additional memory can be implemented into the system 202, such as being attached to the bus 204 as one of the other respective modular components 206. Thus the amount of memory and storage capability of the system 202 is quite extensible.

The data controller 210 also includes a data collection control function 216. The data collection control 216 can be a set of one or more program modules, functions or routines programmed to asynchronously retrieve data from the modules 206. In particular, the data collection module 216 includes a memory storage control 218 that controls the overall scheme employed by the master module 200 for accessing the respective modules 206 and retrieving data therefrom. The memory storage control 218 can issue one or more requests to each of the respective modules 206 such as to obtain information from such modules, which can include housekeeping data, biometric data or a combination of data types. As described herein, each of the modules or components 206 may be programmed and configured to acquire different types of biometric data or to control delivery of a therapy. Consequently, each of the respective modules may acquire data at a different rate such that the available memory within each of the corresponding modules may fill at different respective rates. Since the master module can know the type of a given module 206 and based upon the type of modules the amount of available memory for storing biometric data, the master module can send requests for certain housekeeping data from each of the modules based on which it can determine the relative fullness of the modules. In order to issue these and other requests, the data collection control 216 includes a request engine 220 that is configured to employ the bus interface 212 for sending requests over the bus to one or more these modules 206.

As an example, the request engine 220 can packetize a request to an address associated with a given module or a broadcast request to the set of modules connected to the bus 204. A request may include data or instructions calling for certain information, such as housekeeping information that may be contained in a memory structure that is different from the memory structure stored in the biometric data for the given module 206. As described herein, for example, the request can include a request for housekeeping information that includes a counter value indicative of a location or an index associated with the biometric data stored in a corresponding memory at each respective module 206. Thus, in response to such request, each modular component 206 can send a response with the requested information, including a counter value indicative a location that can be utilized to ascertain an address or location for biometric data in a corresponding memory structure. The response is sent from the modular component 206 over the bus 204.

The bus interface 212 of the data controller 210 provides the responses to a response engine 222. The response engine 222 handles responses received from the modules such that the data collection control 216 can process the responses in a corresponding order. For example, the data collection control 216 can include a fullness calculation module 224 that is programmed to ascertain a relative fullness of the biometric data in a respective module based on the information contained in a response to the corresponding request. As described herein, for example, the response can include a counter value based on which the fullness calculator 224 can ascertain the relative fullness of the memory structure for storing biometric data in each of the respective modular components 206. The relative fullness may be an absolute fullness that depends on a predefined capacity of the memory in each module. The relative fullness calculator may also be programmed to determine a rate at which a respective memory structure is being filled such as can be determined based upon other response information including the number of active channels at a given modular component and the sampling rate of data at a given modular component. Those skilled in the art will understand and appreciate various ways and calculations that can be performed by the fullness calculator 224 based upon housekeeping data returned in a response from a given modular component.

The data collection control 216 further may include a prioritization engine 226. The prioritization engine 226 can be programmed to prioritize further requests for biometric data for each of the respective modular components 206. The prioritization can vary according to the intended purpose of the biometric monitoring system 202. The prioritization further may be performed based on the relative fullness of the memory structure storing the biometric data in each of the respective modular components 206. The prioritization engine may also (or additionally) determine the priority according to the type of each of the plurality of data acquisition modules and patient specific parameters (e.g., condition of the patient, purpose for the monitoring, as well as other variables associated with the patient). The priority can be a weighted priority that is set as a function of the type of module and the amount of data acquired per data acquisition sequence at the module and based on the patient specific parameters.

The prioritization engine 226 (or other process) can determine if a request for biometric data is necessary based upon the fullness determined by the fullness calculator 224 for each of the respective modular components 206, and if it is determined that a request for biometric data should be made, the prioritization engine can prioritize the request for biometric data so that requests are first sent out to higher priority modular components so that the resulting responses and associated data are received from such higher priority components. For example, certain biometric conditions being monitored may be considered high priority conditions such as pulse rate, brain activity, and the like where as other condition may be considered lowered priority, such as monitoring activation of muscular tissue. Thus, those skilled in the art will understand and appreciate various routines and combinations of information that can be utilized to implement appropriate controls prioritizing requests and responses for biometric data.

As a further example, the memory 214 can store modular configuration data at 228 and biometric data 230 for each of the respective modular components. For example, during an initialization or calibration phase, the data collection control 216 can send a request to each of the physical locations or physical addresses at which each of the modular components are connected to the bus 204. Such requests can include data or instructions calling for return of modular configuration information for each modular component, which can result in corresponding responses being sent to the master module 200. The module configuration information can in turn be stored as the module configuration data 228 at the monster module. The module configuration data 228 thus can be utilized to ascertain the type or function of the given module as well as the particular configuration thereof. For example, module configuration data for a given module may include (or the master module may derive the following information from the module configuration data): the memory available for storing biometric data, a level of priority associated with the module or component, data sampling rates, the number of active channels and other configuration information that may be useful in determining what information is stored in the modular component 206. Thus, the data collection control 216 can determine a relative fullness of memory in each modular component based on the configuration data 228 and updated indicator data (e.g., a counter value as described herein) retrieved from the modular component to asynchronously acquire biometric data from the modular components 206 in the system 202.

Biometric data received by the response engine 222 further can be stored by the data controller 210 into the memory 214 as the biometric data 230. Thus, the memory 214 in the master module can store a set of biometric data 230 for each of the respective modular components 206. Additionally, the master module 200 can process data from one or more modules and store processed sets of data in the memory. Since certain modules may acquire data at a greater rate than others, the amount of memory allocated for a given module can vary according to its intended purpose. It would further be appreciated as described herein, that one or more other modular components 206 can be memory modules for storing additional biometric data or other data associated with operation of the system 202.

As the available memory 214 in the master module 200 or associated modular component 206 is nearing its capacity, the master module can be programmed to transmit the data or indicate a signal (e.g., audible or visual or a combination thereof) that can be utilized for triggering a download of data from the biometric monitoring system 202 to another device. It should be understood and appreciated that the amount of memory available in the system 202 can be sufficient to allow use over an extended period of time for monitoring a number of biometric conditions. The download of information from the biometric monitoring system 202 to another device (e.g., a client or service) can be performed in a variety of ways, such as described herein.

FIG. 4 depicts a perspective view of one example embodiment of a modular system 300 that can be constructed in accordance with an aspect of the invention. The modular system 300 includes a plurality of modular apparatuses 302 configured for performing desired functions such as described herein. For example, by replacing, inserting, swapping a set of one or more modular apparatuses 302, the modular system 300 can be configured to operate for acquisition of particular biometric data, control delivery of desired therapy and/or transmit data based on a particular transmission protocol. As one example, one or the modular apparatuses 302 in the modular system 300 can be adapted to acquire data related to electromyography (EMG, e.g., at frequency range 2-500 Hz), another can acquire electrocardiography data (ECG, e.g., at frequency range 0.05-100 Hz, and resolution of 24 bits), another may acquire electroencephalography data (EEG, e.g., frequency range 0.16-100 Hz), while another module may acquire blood pressure data, and other modules may acquire data indicative of joint angle, pulse oximetry and the like. Each of the modular apparatuses 302 can be connected to corresponding sensor(s) via an appropriate connector 304.

Each of the modular apparatuses 302 further can include one or more channels for acquiring and processing input signals indicative of corresponding biometric conditions. Each channel of each modular apparatus, for example, provides data that can be sampled at an appropriate data acquisition rate. Due to the different types and functions of the modular apparatuses the sampling rates can vary significantly. The number of channels and sampling rates thus determine the rate of data storage for each respective modular apparatus 302. The sampling rates further may change during normal operation depending on a variety of factors such as described herein. For instance, asynchronous data collection can be implemented across modular apparatuses 302, while at the same time employing a synchronous clock within each modular apparatus to provide timing on module for local data collection functions. Due to the wide range of potential types of modular apparatuses that can be implemented and corresponding varying rates that data may be stored in the memory at such modules, the master module can collect data asynchronously from each of the modular apparatuses depending on a relative fullness of the respective memory for such modules.

Figure 5:
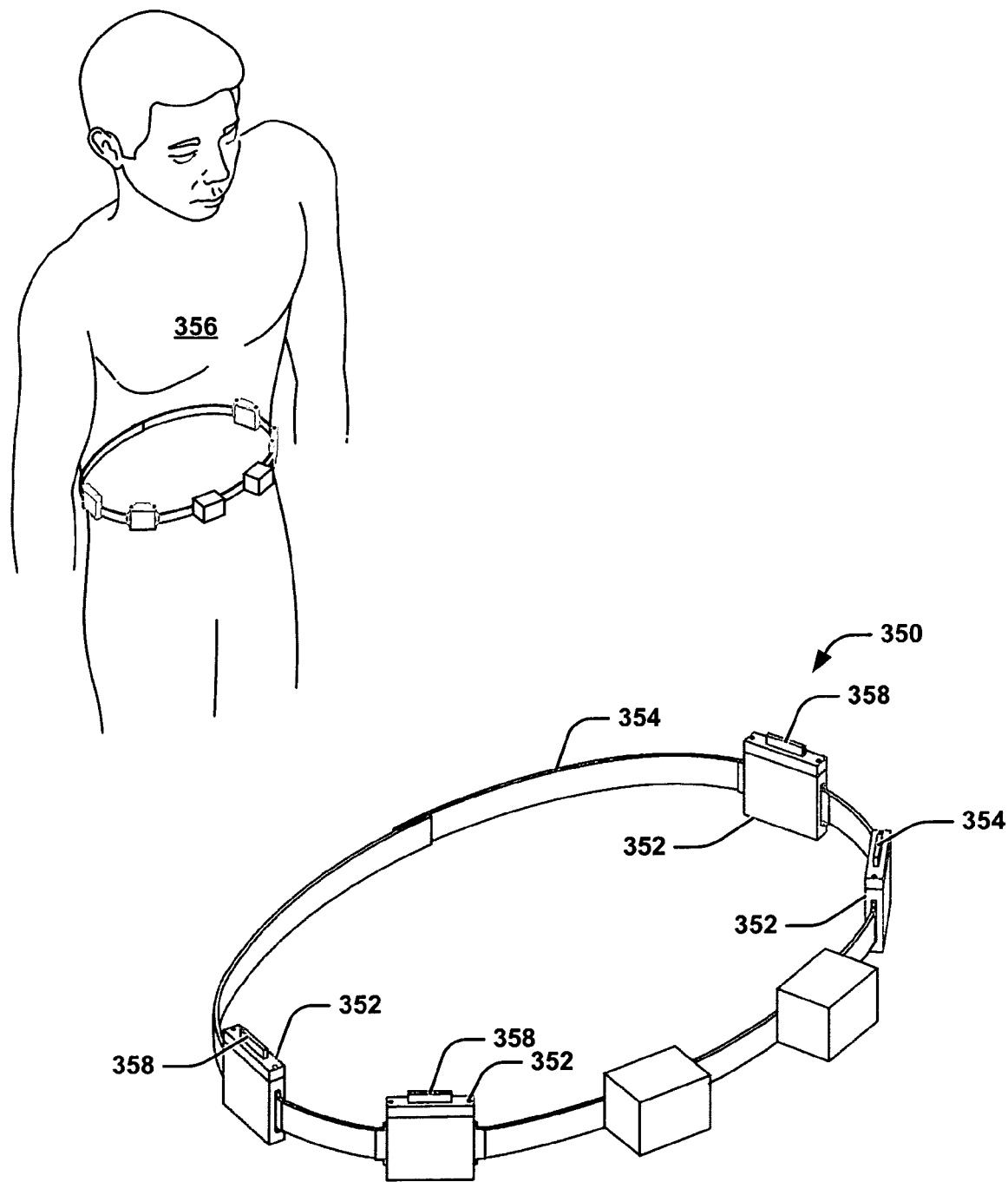
FIG. 5 depicts another example of a modular system that can be implemented according to an aspect of the present invention.

FIG. 5 depicts another embodiment of a modular system 350 that can be implemented according to an aspect of the invention. In the example of FIG. 5, the modular system 350 includes a plurality of modular apparatuses 352 spatially distributed along a common communication link (or bus) 354, such as can be implemented as part of a belt or harness attached to or disposed around the body of a user. While the communication link 354 is depicted as a belt in the example of FIG. 6, other types of harnesses (e.g., a chest harness, wrist band, arm band, a hat or the like) could be implemented. Certain modular apparatuses 352 can thus be located proximate to predetermined portions of a patient's body 356. Data can be communicated with such modular components 352 over a common communication link, or network, wherein all modules on the network communicate via a standard communications protocol. At least some of the modular apparatuses 352 include a modular component 358, which can be replaced, inserted or swapped for desired operation. Each modular component 358 has a form factor configured according to the requirements and interface provided at the apparatus 352.

In such a distributed system, one or more I/O modules are provided for interfacing with a process, wherein the outputs derive their control or output values in the form of a message from a master controller over the bus 354. For example, a modular component can receive a request or instruction a processor, via a communications network or a backplane communications bus. The desired output value for controlling a device associated with a given biometric condition can be generally sent to the output module in a message, such as an I/O message (e.g., a request or a response). The modular component that receives such a request message can provide a corresponding output response (analog or digital) to the controlled process. The modular component can also measure a value of a process variable and report the input values to a master controller or peer modular component over the network or bus 354. The master module can control data collection from the modular components to be asynchronous based on the fullness of determined for predetermined memory in each of the respective modular components. The input values may be used by the master module for performing control computations.

Figure 6:
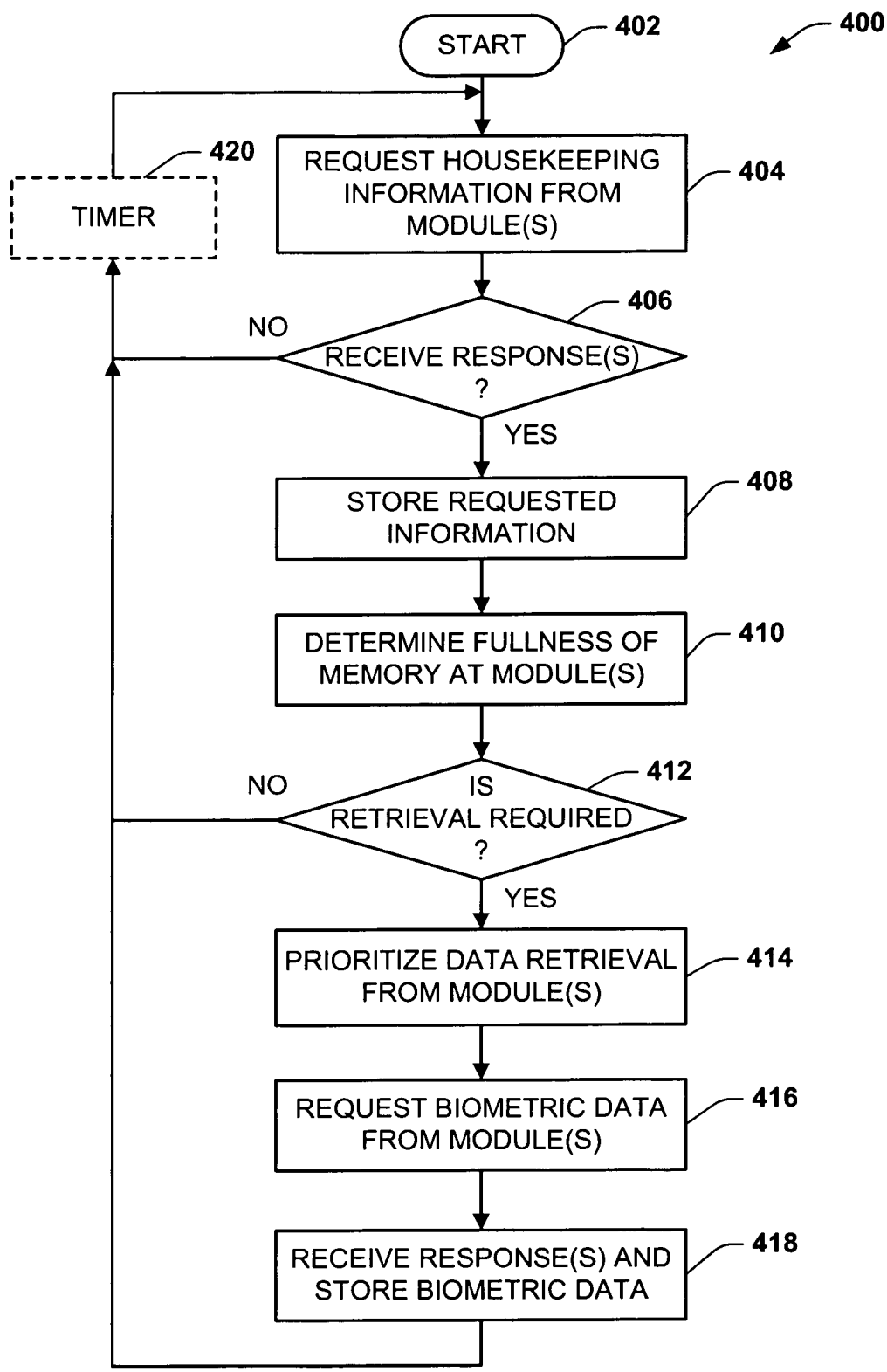
FIG. 6 is a flow diagram illustrating a method that can be utilized to collect data in a biometric monitoring system according to an aspect of the invention.
Figure 7:
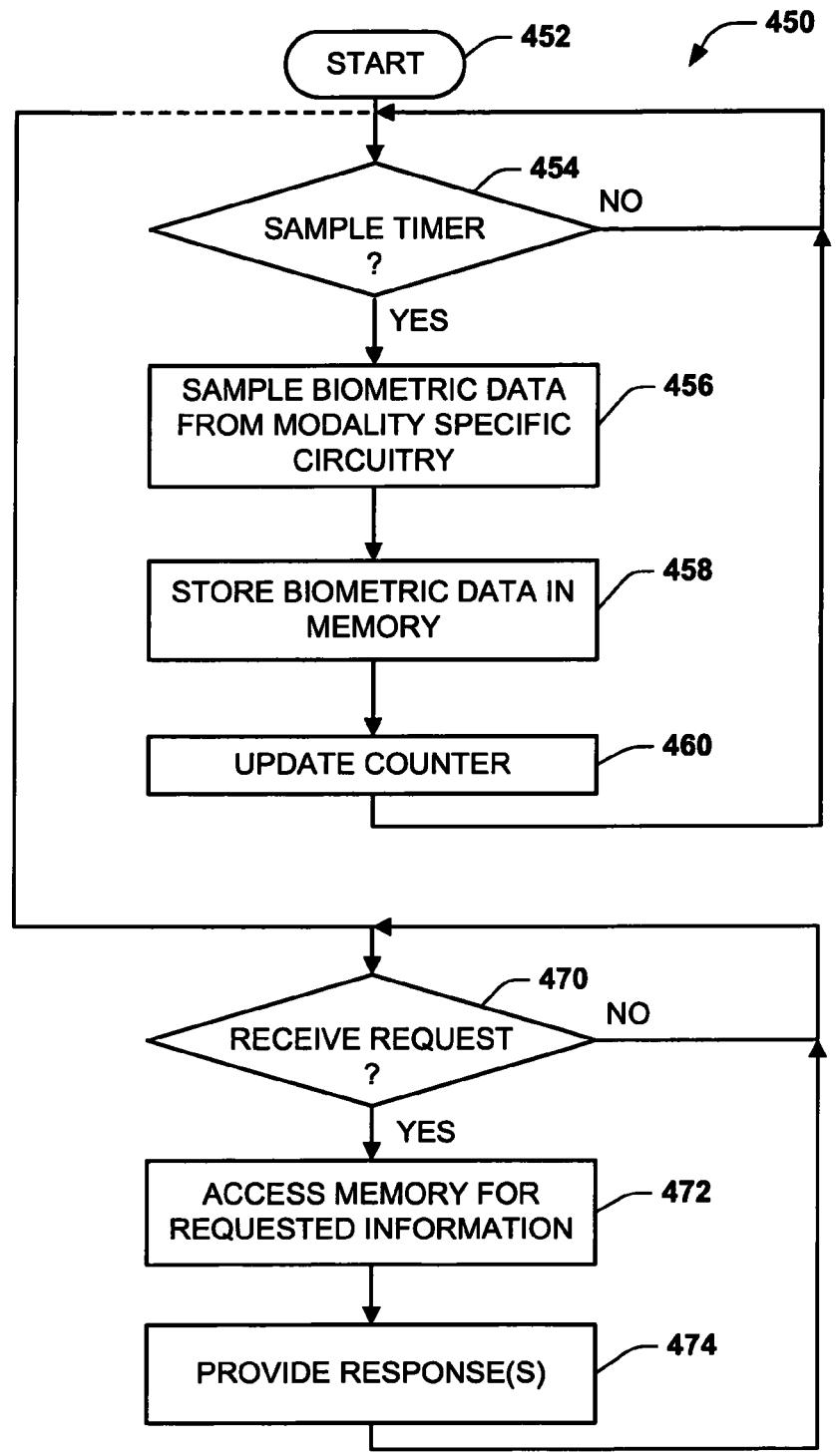
FIG. 7 is a flow diagram illustrating a method that can be utilized acquiring data as well as for communicating data in a biometric monitoring system according to an aspect of the invention.

In view of the structural and functional features described above, certain methods will be better appreciated with reference to FIGS. 6 and 7. It is to be understood and appreciated that the illustrated actions, in other embodiments, may occur in different orders or concurrently with other actions. Moreover, not all features illustrated in FIGS. 6 and 7 may be required to implement a method according to the subject invention. It is to be further understood that the following methodology can be implemented in hardware (e.g., one or more processors, such as in a computer or computers or in a biomedical device), software (e.g., stored in a computer readable medium or as executable instructions running on one or more processors), or as a combination of hardware and software.

FIG. 6 depicts a method 400 for asynchronously retrieving data from one or more modules, such as may form part of a biometric monitoring system according to an aspect of the invention. The method 400 may be implemented within a master module or other module that may be programmed to retrieve or collect biometric data from one or more modules. As described herein, the biometric data may include sensed data from one or more modules as well as feedback and other information associated with the control or delivery of a therapy to a patient.

The method begins at 402 such as in conjunction with power-up. Power-up can include initialization of program parameters and loading operating instructions, such as may be programmed to perform a particular task. The task may include a variety of one or more functions associated with monitoring one or more biometric conditions, delivering therapy to a patient or a combination thereof. The method proceeds to 404 in which housekeeping information is requested from one or more modules. The housekeeping information can include a variety of information including but not limited to module configuration information, module identification information, control information, sampling intervals, number of active channels and the like.

At 406 a determination is made as to whether a response to the request (at 404) is received. If no response is received, the method may return to 404 for re-requesting such information. Alternatively, a timer or time up process may be implemented in which a request must receive a response within the predetermined time period or the request times out. If the request is timed out, it may be repeated or other action may be taken in the event of an error. If a response is received from 406 the method proceeds to 408.

At 408, the requested information from the received response is stored in memory. The memory can be local memory, such as in the master module or remote memory such as may be located in another module of a biometric monitoring system. At 410, the fullness of the memory at the module is determined based upon the stored information. For example, the fullness of the memory can be determined based on a counter value (individually or in combination with other data) provided in the response received at 406 from a remote module. The counter value can indicate a location in memory at the module relative to knowing the available amount of memory for storing such information. The fullness of the memory thus can be derived as an indication of how much biometric data has been stored in the available memory and/or a determination of how much memory space remains for storing biometric data at the respective module. The fullness determination can be made for one or more of the modules in the biometric monitoring system based on corresponding responses received at 406.

At 412, a determination is made as to whether retrieval of biometric data is required. If the determination at 412 is negative, indicating retrieval is not required the method may return to 404. If it is determined that retrieval is required the method may proceed to 414. At 414, the data collection process from the respective modules can be prioritized. The prioritization can be based on a number of factors, including the relative fullness of memory at the modules, a predetermined relative importance of the type of biometric information being acquired at each of the respective modules as well as other criteria that may be associated with the intended purpose or function(s) being performed by the biometric monitoring system.

At 416, biometric data can be requested from one or more modules for which it has been determined (at 412) that retrieval is required. The request can be issued to the address of each module over a corresponding data bus such as described herein. At 418, responses can be received from each of the respective modules including the requested biometric data. The corresponding biometric data can be extracted from the corresponding responses and stored in memory, such as local memory at the master module or at some other location at the biometric monitoring system. The master module can perform a variety of functions relative to the stored information which can be utilized to provide useful information about the condition of the patient as well as about the status or health of the respective modules. For example, can the master module can compute values based on biometric data received from one module or based on an aggregate set of such data received from multiple modules. From 418, the method proceeds to 420 corresponding to a timer function that can be utilized to control the frequency at which the housekeeping information is requested from the respective modules. Similarly, each of the decisions at 406 and 412 may also return to 404 through the timer function 420 to control when housekeeping information may be requested from the modules. The timing between requests can be the same for all modules or it may vary depending on the type or configuration of the respective modules. Thus, it will be appreciated that the biometric data can be requested asynchronously from the modules where the modules may acquire data synchronously at various rates according to the type of information being acquired by each respective module.

FIG. 7 is a flow diagram depicting a method 450 for certain functionality that may be implemented at a given module in a biometric monitoring system according to an aspect of the invention. In a typical system, each module can thus implement a method similar to the method 450, which further may vary in implementation according to the modality of such module. The method 450 begins at 452 such as may occur at power-up or upon attachment of a module to a backplane or bus in the biometric monitoring system. This can include registration with a master module, setting start parameters to their starting values and other initialization processes that may be implemented for the module.

At 454, a determination is made as whether a sampling timer has expired. The sampling timer can be set to provide a data acquisition rate for the modality specific circuitry in the given module. The sample rate can be fixed for a given module or it may vary depending on an operating mode of the module and a module can have any number of operating modes. If the sample timer has not expired at 454, the sampling can remain idle (e.g., and channel data can be buffered or discarded) during the operation of the modality specific portion of the module. Once the sampling timer expires, indicating data acquisition is required, the method proceeds to 456. At 456, the biometric data is sampled from the modality simple circuitry. As described herein, the sample data may include a digital representation of channel data from any number of one or more channels. The number of channels and amount of data stored for each channel may vary depending upon the type and configuration of the module and the purpose of monitoring system. Additionally, the biometric data may include information associated with the delivery of a given therapy or other conditions.

At 458, the sampled biometric data is stored in memory of the biometric monitoring device. This memory can be a different structure form the memory structure employed to store housekeeping information. The housekeeping information can include information associated with the health of a given module, its configuration and other information such as described herein. At 460, a counter is updated responsive to the storing of the biometric data in the memory. The counter can be part of the housekeeping information that is utilized to provide an index or other indication relating to the location in the memory where the biometric data has been stored. As a further example, another process running the biometric monitoring system (e.g., at a master module) may employ the counter value as an index or address provided in a request (or other message) to retrieve the stored biometric data from the module implementing the method 450. From 460, the method returns to 454 to continue the data acquisition process.

Also depicted in FIG. 7 is a basic process for handling a request and providing responses for data in the given module. This process may run in parallel with or in series with the data acquisition process described at 454 to 460.

At 470, a determination is made as to whether a request is received. The request can be received, for example, from a data bus to which the given module is connected through a bus interface. If no request is received, the module may loop at 470. The module may periodically check for requests via the bus. If a request is received (Yes) the method proceeds from 470 to 472. The requested information for example can include a request for information such as biometric data, housekeeping data, or other information that may be maintained at the given module. The data can be access from one or more memory structure residing in the given module and, at 474, one or more responses can be provided. For example, certain information may be submitted in a single packet from the module to the requester, whereas other information may require multiple packets to be sent over the bus to complete a given response. Those skilled in the art will understand and appreciate that the number of packets and manner in which the data is sent over the bus can vary depending upon the configuration of the bus architecture and the protocol utilized for data transmission. From 474, the method can return to 470 for processing additional requests.

Although the innovation has been shown and described with respect to certain illustrated aspects, it will be appreciated that equivalent alterations and modifications will occur to others skilled in the art upon the reading and understanding of this specification and the annexed drawings. In particular regard to the various functions performed by the above described components (assemblies, devices, circuits, systems, etc.), the terms (including a reference to a "means") used to describe such components are intended to correspond, unless otherwise indicated, to any component which performs the specified function of the described component (e.g., that is functionally equivalent), even though not structurally equivalent to the disclosed structure, which performs the function in the herein illustrated exemplary aspects of the innovation. Furthermore, to the extent that the terms "includes", "including", "has", "having", and variants thereof are used in either the detailed description or the claims, these terms are intended to be inclusive in a manner similar to the term "comprising."

What is claimed is:
1. A modular biometric monitoring system comprising:
a plurality of data acquisition modules configured to sample biometric data for a predetermined type of biometric condition from at least one respective input channel at a data acquisition rate, a representation of the sampled biometric data being stored in memory of each of the plurality of data acquisition modules, each of the plurality of data acquisition modules being configured to store housekeeping data in the memory, the housekeeping data comprising a value indicative of an amount of biometric data stored in the memory of each respective data acquisition module; and a central control system in communication with each of the plurality of data acquisition modules through a bus, the central control system being configured to collect data asynchronously, via the bus, from the memory of the plurality of data acquisition modules according to a relative fullness of the memory of the plurality of data acquisition modules determined from the housekeeping data thereof, wherein the central control system further comprises a prioritization engine that determines a priority that establishes at least part of an order from which of the plurality of data acquisition modules the biometric data is collected.

2. The system of claim 1, wherein the memory in each of the plurality of data acquisition modules further comprises:
a first memory structure configured to store biometric data, and
a second memory structure configured to store the housekeeping data, the housekeeping data being changed in response to storing the biometric data in the first memory structure,
the central control system employing the stored housekeeping data retrieved from the second memory structure of a given one of the plurality of data acquisition modules to determine the relative fullness of the memory in the given one of the plurality of data acquisition modules.

3. The system of claim 2, wherein each of the first memory structure and the second memory structure comprises a respective first-in-first-out (FIFO) data structure.

4. The system of claim 2, wherein the second memory structure of each of the plurality of data acquisition modules further comprises a counter that is updated in response to storing the representation of the sampled biometric data in the first memory structure of each of the plurality of data acquisition modules.

5. The system of claim 4, wherein the counter is updated by being incremented an amount commensurate with an amount of the sampled biometric data that is stored in the first memory structure of each of the plurality of data acquisition modules, the counter having a value that defines at least one of an amount or a location of the biometric data stored in the first memory structure.

6. The system of claim 4, wherein the central control system is programmed to determine the relative fullness of the first memory structure in each of the plurality of data acquisition modules based on the housekeeping data stored in the second memory structure including the value of the counter and module configuration information.

7. The system of claim 2, wherein the first memory structure of each of the plurality of data acquisition modules has a capacity that is defined according to a type of the biometric data to be acquired by the respective data acquisition module and the data acquisition rate thereof.

8. The system of claim 1, wherein each of the plurality of data acquisition modules further comprises a counter having a value that is updated in response to storing the representation of the sampled biometric data in the memory thereof, the central control system retrieving data indicative of the value of the counter for each of the plurality of data acquisition modules and determining the relative fullness of the memory in each of the plurality of data acquisition modules based at least in part on the value of the counter for each respective data acquisition module.

9. The system of claim 8, wherein the counter of each of the plurality of data acquisition modules is incremented an amount commensurate with an amount of the sampled biometric data that is stored in the memory thereof for a given sampling interval, the value of the counter being indicative of an address location of the biometric data that is stored in the memory for each of the plurality of data acquisition modules, the central control system being programmed to determine the relative fullness of the memory in each of the plurality of data acquisition modules according to the value of the counter and a previously defined capacity for each of the plurality of data acquisition modules.

10. The system of claim 9, wherein the central control system determines the relative fullness of the memory in each of the plurality of data acquisition modules based on a change in the value of the counter from a comparison of a preceding counter value of the counter relative to a subsequent counter value.

11. The system of claim 1, wherein the prioritization engine determines the priority according to at least two of: (i) the relative fullness of the memory of each of the plurality of data acquisition modules, (ii) a type of each of the plurality of data acquisition modules and (iii) patient specific parameters.

12. The system of claim 11, wherein the priority is a weighted priority that is set as a function of the type of module and an amount of data acquired per sequence and the patient specific parameters.

13. The system of claim 1, wherein each of the plurality of data acquisition modules comprises a form factor configured to enable replacement or swapping of modules into and out of communication with the bus.

14. A biometric monitoring system comprising:
a plurality of modular components configured to sample a predetermined type of biometric data received from at least one respective input channel according to a data acquisition rate, each of the plurality of modular components comprising:
a first memory structure configured to store housekeeping information associated with operation of the respective modular component, and
a second memory structure configured to store a representation of the sampled biometric data, the housekeeping information in the first memory structure comprising data indicative of an amount of biometric data stored in the second memory structure and being updated in response to storing the representation of the sampled biometric data in the second memory structure; and
a master module configured to retrieve data asynchronously, via a bus to which each of the plurality modular components is connected, from the second memory structure of the plurality modular components according to a relative fullness of the second memory structure in each of the plurality modular components as determined by the master module based on the updated housekeeping information in the plurality of modular components,
wherein the master module further comprises a prioritization engine that determines a priority for establishing an order from which of the plurality of modular components that data is collected by the master module.

15. The system of claim 14, wherein the housekeeping information stored in the first memory structure of each of the plurality of modular components further comprises a counter having a value that is updated in response to storing the representation of the sampled biometric data in the first memory structure of each of the plurality of modular components.

16. The system of claim 15, wherein the value of the counter is incremented an amount commensurate with an amount of the sampled biometric data that is stored in the second memory structure of each of the plurality of modular components.

17. The system of claim 15, wherein the master module is programmed to send a request for retrieving the biometric data from a given modular component of the plurality of modular components, the request to the given modular component including address data corresponding to the value of the counter to facilitate access and retrieval of the biometric data from the second memory structure of the given modular component.

\* \* \* \* \*